(12) United States Patent
Gerring et al.

(10) Patent No.: US 11,278,624 B2
(45) Date of Patent: Mar. 22, 2022

(54) FORMULATIONS

(71) Applicant: Arecor Limited, Saffron Walden (GB)

(72) Inventors: David Gerring, Saffron Walden (GB); Leon Zakrzewski, Saffron Walden (GB); Jan Jezek, Saffron Walden (GB); Sarah Howell, Saffron Walden (GB)

(73) Assignee: ARECOR LIMITED, Saffron Walden (GB)

( * ) Notice: Subject to any disclaimer, the term of this patent is extended or adjusted under 35 U.S.C. 154(b) by 0 days.

(21) Appl. No.: 15/720,017

(22) Filed: Sep. 29, 2017

(65) Prior Publication Data

US 2018/0078645 A1  Mar. 22, 2018

Related U.S. Application Data

(63) Continuation-in-part of application No. PCT/GB2017/051254, filed on May 5, 2017.

(30) Foreign Application Priority Data

May 6, 2016 (GB) ..................................... 1607918

(51) Int. Cl.
| | | |
|---|---|---|
| A61K 47/18 | (2017.01) | |
| A61K 38/28 | (2006.01) | |
| A61K 47/10 | (2017.01) | |
| A61K 47/26 | (2006.01) | |
| A61K 9/08 | (2006.01) | |
| A61M 5/00 | (2006.01) | |
| A61K 33/30 | (2006.01) | |
| A61K 9/00 | (2006.01) | |
| A61K 47/12 | (2006.01) | |
| A61M 5/178 | (2006.01) | |

(52) U.S. Cl.
CPC .......... *A61K 47/183* (2013.01); *A61K 9/0019* (2013.01); *A61K 9/08* (2013.01); *A61K 33/30* (2013.01); *A61K 38/28* (2013.01); *A61K 47/10* (2013.01); *A61K 47/12* (2013.01); *A61K 47/26* (2013.01); *A61M 5/00* (2013.01); *A61M 5/178* (2013.01)

(58) Field of Classification Search
USPC ........................................................ 549/531
See application file for complete search history.

(56) References Cited

U.S. PATENT DOCUMENTS

| | | |
|---|---|---|
| 5,866,538 A | 2/1999 | Norup et al. |
| 6,960,561 B2 | 11/2005 | Boderke |
| 7,205,276 B2 | 4/2007 | Boderke |
| 7,279,457 B2 | 10/2007 | Pohl et al. |
| 7,452,860 B2 | 11/2008 | Boderke |
| 7,476,652 B2 | 1/2009 | Brunner-Schwarz et al. |
| 7,696,162 B2 | 4/2010 | Boderke |
| 7,998,927 B2 | 8/2011 | Maggio |
| 8,318,154 B2 | 11/2012 | Frost et al. |
| 8,772,231 B2 | 7/2014 | Maggio |
| 9,833,516 B2 | 12/2017 | Lim et al. |
| 2005/0214251 A1 | 9/2005 | Pohl et al. |
| 2006/0287221 A1 | 12/2006 | Knudsen et al. |
| 2007/0298010 A1 | 12/2007 | Maggio |
| 2008/0039365 A1 | 2/2008 | Steiner et al. |
| 2008/0194461 A1 | 8/2008 | Maggio |
| 2009/0011976 A1 | 1/2009 | Ludvigsen et al. |
| 2009/0137455 A1 | 5/2009 | Steiner et al. |
| 2010/0210506 A1 | 8/2010 | Quay et al. |
| 2010/0227795 A1 | 9/2010 | Steiner et al. |
| 2010/0249020 A1 | 9/2010 | Soula et al. |
| 2011/0097348 A1* | 4/2011 | Jezek ..................... C07K 14/00 424/184.1 |
| 2012/0135920 A1* | 5/2012 | Olsen ....................... A61P 9/10 514/6.3 |
| 2012/0178675 A1 | 7/2012 | Pohl et al. |
| 2013/0231281 A1 | 9/2013 | Adocia |
| 2013/0302275 A1* | 11/2013 | Wei ....................... A61K 38/28 424/85.2 |
| 2013/0331320 A1 | 12/2013 | Havelund et al. |
| 2014/0024582 A1 | 1/2014 | Yang |
| 2014/0135263 A1 | 5/2014 | Pohl et al. |
| 2014/0142034 A1 | 5/2014 | Soula et al. |
| 2014/0357554 A1 | 12/2014 | Pohl et al. |
| 2015/0190475 A1* | 7/2015 | Bley ..................... A61K 9/0019 514/6.4 |
| 2015/0231160 A1 | 8/2015 | Soula et al. |
| 2015/0265683 A1 | 9/2015 | Sahib et al. |
| 2015/0273022 A1* | 10/2015 | Wilson .................. A61K 38/28 424/682 |

(Continued)

FOREIGN PATENT DOCUMENTS

| | | |
|---|---|---|
| CA | 2441260 A1 | 10/2002 |
| EP | 0214826 A2 | 3/1987 |

(Continued)

OTHER PUBLICATIONS

Mahmoudi Moghaddam et al. (Evaluation of Insulin Stability in the Presence of Nonionic Surface Active Agents (Polysorbate Groups) by Circular Dichroism and Fluorescence Spectroscopy. Asian Journal of Biochemistry, 2015, 10(1): 17-30).*

Lougheed, W. D., et al., "Physical Stability of Insulin Formulations," Diabetes 32:424-432 (1983).

Moghaddam, H. M., et al., "Evaluation of Insulin Stability in the Presence of Nonionic Surface Active Agents (Polysorbate Groups) by Circular Dichroism and Fluorescence Spectroscopy," Asian Journal of Biochemistry 10(1):17-30 (2015).

Sluzky, V., et al., "Mechanism of Insulin Aggregation and Stabilization of Agitated Aqueous Solutions," Biotechnology and Bioengineering 40:895-903 (1992).

(Continued)

*Primary Examiner* — Maury A Audet
(74) *Attorney, Agent, or Firm* — Nixon & Vanderhye P.C.

(57) ABSTRACT

According to the invention there is provided inter alia an aqueous liquid pharmaceutical formulation comprising insulin or an insulin analogue, ionic zinc, a chelating agent and polysorbate 80.

24 Claims, No Drawings

Specification includes a Sequence Listing.

(56) References Cited

U.S. PATENT DOCUMENTS

2018/0161448 A1 6/2018 Heo et al.

FOREIGN PATENT DOCUMENTS

| EP | 0375437 A2 | 6/1990 |
|---|---|---|
| EP | 0678522 A1 | 10/1995 |
| EP | 1283051 A1 | 2/2003 |
| EP | 1381385 B1 | 1/2004 |
| EP | 1740154 B1 | 1/2007 |
| EP | 2106790 B1 | 10/2009 |
| EP | 2289539 B1 | 3/2011 |
| EP | 2319500 B1 | 5/2011 |
| EP | 2340033 B1 | 7/2011 |
| GB | 786635 A | 11/1957 |
| WO | WO-9109617 A1 | 7/1991 |
| WO | WO-9610417 A1 | 4/1996 |
| WO | WO-9717945 A2 | 5/1997 |
| WO | WO-9934821 A1 | 7/1999 |
| WO | WO 2000/023098 A1 | 4/2000 |
| WO | WO 2002/076495 A1 | 10/2002 |
| WO | WO-02076495 A1 | 10/2002 |
| WO | WO 2003/105888 A1 | 12/2003 |
| WO | WO 2004/080480 A1 | 9/2004 |
| WO | WO 2005046716 A1 | 5/2005 |
| WO | WO 2005/089722 A1 | 9/2005 |
| WO | WO-2005089722 A1 | 9/2005 |
| WO | WO 2006/082245 A1 | 8/2006 |
| WO | WO 2007/041481 A1 | 4/2007 |
| WO | WO-2007041481 A1 | 4/2007 |
| WO | WO-2007121256 A2 | 10/2007 |
| WO | WO-2007149096 A1 | 12/2007 |
| WO | WO-2008084237 A2 | 7/2008 |
| WO | WO 2008/132229 A2 | 11/2008 |
| WO | WO 2009/115469 A1 | 9/2009 |
| WO | WO-2009134380 A2 | 11/2009 |
| WO | WO 2010/028055 A1 | 3/2010 |
| WO | WO-2010102020 A1 | 9/2010 |
| WO | WO-2010115819 A1 | 10/2010 |
| WO | WO-2010149772 A1 | 12/2010 |
| WO | WO 2011086093 A2 | 7/2011 |
| WO | WO-2011094632 A1 | 8/2011 |
| WO | WO 2011/144673 A2 | 11/2011 |
| WO | WO 2012/006283 A1 | 1/2012 |
| WO | WO-2012006283 A1 | 1/2012 |
| WO | WO-2013021143 A1 | 2/2013 |
| WO | WO 2013/158618 A1 | 10/2013 |
| WO | WO-2013158618 A1 | 10/2013 |
| WO | WO-2013186138 A1 | 12/2013 |
| WO | WO 2014/017847 A1 | 1/2014 |
| WO | WO 2014017849 A1 | 1/2014 |
| WO | WO 2014/118355 A1 | 8/2014 |
| WO | WO 2014/161837 A1 | 10/2014 |
| WO | WO 2015/059302 A1 | 4/2015 |
| WO | WO-2015059302 A1 | 4/2015 |
| WO | WO 2015104314 A1 | 7/2015 |
| WO | WO 2015/120457 A1 | 8/2015 |
| WO | WO-2015114374 A1 | 8/2015 |
| WO | WO-2015120457 A1 | 8/2015 |
| WO | WO-2015171484 A1 | 11/2015 |
| WO | WO 2015173427 A2 | 11/2015 |
| WO | WO 2016/100042 A1 | 6/2016 |
| WO | WO-2016100042 A1 | 6/2016 |
| WO | WO 2017034956 A1 | 3/2017 |
| WO | WO-2018060735 A1 | 4/2018 |
| WO | WO-2018060736 A1 | 4/2018 |
| WO | WO-2018203059 A1 | 11/2018 |
| WO | WO-2018203060 A2 | 11/2018 |
| WO | WO-2018203061 A1 | 11/2018 |
| WO | WO 2019020820 A2 | 1/2019 |
| WO | WO-2019193349 A1 | 10/2019 |
| WO | WO-2019193351 A1 | 10/2019 |
| WO | WO-2019193353 A1 | 10/2019 |

OTHER PUBLICATIONS

"2.9.20. Particulate Contamination: Visible Particles," European Pharmacopoeia Monograph p. 302 (2008).

Arnebrant, T. and Nylander, T., "Adsorption of Insulin on Metal Surfaces in Relation to Association Behavior," Journal of Colloid and Interface Science 122(2):557-566 (1988).

Cooper, G. J. S., "Therapeutic potential of copper chelation with triethylenetetramine in managing diabetes mellitus and Alzheimer's disease," Drugs, Medline/NLM AB 71(10):XP002774649 (ABSTRACT)(2011).

Liu, F., et al., "Insulin Aggregation in Aqueous Media and Its Effect on Alpha-Chymotrypsin-Mediated Proteolytic Degradation," Pharmaceutical Research 8(7):925-929 (1991).

Okada, H., et al., "Vaginal Absorption of a Potent Luteinizing Hormone-Releasing Hormone Analogue (Leuprolide) in Rats II: Mechanism of Absorption Enhancement with Organic Acids," Journal of Pharmaceutical Sciences 72(1):75-78 (1983).

Pillai, O., et al., "Transdermal iontophoresis of insulin II. Physicochemical considerations," International Journal of Pharmaceutics 254:271-280 (2003).

Pohl, R., et al., "Ultra-Rapid Absorption of Recombinant Human Insulin Induced by Zinc Chelation and Surface Charge Masking," Journal of Diabetes Science and Technology 6(4):755-763(2012).

Prabhu, S., et al., "A study of factors controlling dissolution kinetics of zinc complexed protein suspensions in various ionic species," International Journal of Pharmaceutics 217:71-78 (2001).

Steiner, S., et al., "A novel insulin formulation with a more rapid onset of action," Diabetologia 51(9):1602-1606 (2008).

Nozawa, et al., "Mind the buffering capacity of citric acid," Jul. 5, 2009, www @ fgsc.net/fgn42/nozawa.html.

Altria, et al., "Buffer Preparation-Hints, Tips and Common Errors," LCGC Asia Pacific 10(2): p. 25, Table 2 (2007), www @ chromatography-online.com/buffer-preparation-hints-tips-and-common-errors-0.

Machine Translation of Intl. Publ. No. WO 2019020820 A2, published Jan. 31, 2019, Applicant: Adocia.

Machine Translation of Intl. Publ. No. WO 2003105888 A1, published Dec. 24, 2003, Applicant: Aventis Pharma Deutschland Gmbh.

Ohiman Ghosh et al., "Structure based aggregation studies reveal the presence of helix-rich intermediate during α-Synuclein aggregation", Scientific Reports, 5: 9228, DOI: 10.1038/srep09228, Mar. 18, 2015, 15 pages.

Martina Pannuzzo et al., "α-Helical Structures Drive Eady Stages of Self-Assembly of Amyloidogenic Amyloid Polypeptide Aggregate Formation in Membranes", Scientific Reports, 3:2781, DOI: 10.1038/srep02781, Sep. 27, 2013, 10 pages.

Marta Owxzarz et al., "Sulfate Anion Delays the Self-Assembly of Human Insulin by Modifying the Aggregation Pathway", Biophysical Journal, vol. 107, Jul. 2014, 17 pages.

* cited by examiner

SEQUENCE LISTING

```
<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25              30

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25              30

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25              30

<210> SEQ ID NO 5
<211> LENGTH: 30
<212> TYPE: PRT
<213> ORGANISM: Homo sapiens

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25              30
```

FORMULATIONS

CROSS-REFERENCE TO RELATED APPLICATIONS

This application is a continuation-in-part of Intl. Appl. No. PCT/GB2017/051254, filed May 5, 2017, which claims priority to GB Pat. Appl. No. 1607918.8, filed May 6, 2016, each of which is incorporated herein by reference in its entirety.

REFERENCE TO SEQUENCE LISTING SUBMITTED ELECTRONICALLY

The content of the electronically submitted sequence listing in ASCII text file (Name: 6662_0012_Sequence_Listing_.txt; Size: 1.67 KB; and Date of Creation: Sep. 28, 2017) filed with the application is herein incorporated by reference in its entirety.

FIELD OF THE INVENTION

This invention relates inter alia to rapid acting aqueous liquid compositions of insulin and insulin analogues. Such compositions are suitable for the treatment of subjects suffering from diabetes mellitus, especially Type I diabetes mellitus.

BACKGROUND OF THE INVENTION

Diabetes mellitus ("diabetes") is a metabolic disorder associated with poor control of blood sugar levels leading to hypo or hyperglycemia. Untreated diabetes can lead to serious microvascular and macrovascular complications including coronary artery disease, peripheral artery disease, stroke, diabetic nephropathy, neuropathy and retinopathy. The two main types of diabetes are (i) Type 1 diabetes resulting from the pancreas not producing insulin for which the usual treatment is insulin replacement therapy and (ii) Type 2 diabetes where patients either produce insufficient insulin or have insulin resistance and for which treatments include insulin sensitising agents (such as metformin or pioglitazone), traditional insulin secretagogues (such as sulfonylureas), SGLT2 inhibitors (such as dapagliflozin, canagliflozin and empagliflozin) which reduce glucose absorption in the kidneys and so promote glucose excretion, GLP-1 agonists (such as exenatide and dulaglutide) which stimulate insulin release from pancreatic beta cells and DPPIV inhibitors (such as sitagliptin or vildagliptin) which inhibit breakdown of GLP-1 leading to increased insulin secretion. Patients with Type 2 diabetes may eventually require insulin replacement therapy.

For patients requiring insulin replacement therapy, a range of therapeutic options are possible. The use of recombinant human insulin has in recent times been overtaken by use of insulin analogues which have modified properties, for example, are longer acting or faster acting than normal insulin. Thus, a common regimen for a patient involves receiving a long acting basal insulin supplemented by a rapid acting insulin around mealtimes.

Insulin is a peptide hormone formed of two chains (A chain and B chain, respectively 21 and 30 amino acids in length) linked via disulfide bridges. Insulin normally exists at neutral pH in the form of a hexamer, each hexamer comprising three dimers bound together by zinc ions. Histidine residues on the insulin are known to be involved in the interaction with the zinc ions. Insulin is stored in the body in the hexameric form but the monomer form is the active form. Traditionally, therapeutic compositions of insulin have also been formulated in hexameric form in the presence of zinc ions. Typically, there are approximately three zinc cations per one insulin hexamer. It has been appreciated that the hexameric form is absorbed from the injection site considerably more slowly than the monomeric and dimeric form. Therefore, a faster onset of insulin action can be achieved if the hexameric form is destabilised allowing a more rapid dissociation of the zinc-bound hexamer into dimers and monomers in the subcutaneous space following injection. Three insulin analogues have been genetically engineered with this principle in mind. A first is insulin lispro (Humalog®) in which residues 28 and 29 of the B chain (Pro and Lys respectively) are reversed, a second is insulin aspart (NovoLog®) in which residue 28 of the B chain, normally Pro, is replaced by Asp and a third is insulin glulisine (Apidra®) in which residue 3 of the B chain, normally Asn, is replaced by Lys and residue 29 of the B chain, normally Lys, is replaced by Glu.

Whilst the existing rapid acting insulin analogues can achieve a more rapid onset of action, it has been appreciated that an even more rapid acting ("ultra rapid acting") insulins can be achieved by removing the zinc cations from insulin altogether. Unfortunately, the consequence of the hexamer dissociation is typically a considerable impairment in insulin stability both with respect to physical stability (e.g. stability to aggregation) and chemical stability (e.g. stability to deamidation). For example, monomeric insulin or insulin analogues having a rapid onset of action are known to aggregate and become physically unstable very rapidly because the formulation of insoluble aggregates proceeds via monomers of insulin. Various approaches to addressing this problem have been described in the art:

U.S. Pat. No. 5,866,538 (Norup) describes insulin preparations of superior chemical stability comprising human insulin or an analogue or derivative thereof, glycerol and/or mannitol and 5 to 100 mM of a halogenide (e.g. NaCl).

U.S. Pat. No. 7,205,276 (Boderke) addresses the stability problems associated with preparing zinc free formulations of insulin and insulin derivatives and analogues and describes an aqueous liquid formulation comprising at least one insulin derivative, at least one surfactant, optionally at least one preservative and optionally at least one of an isotonicizing agent, a buffer and an excipient, wherein the formulation is stable and free from or contains less than 0.4% by weight of zinc based on the insulin content of the formulation. The preferred surfactant appears to be polysorbate 20 (polyoxyethylene (20) sorbitan monolaurate).

US2008/0194461 (Maggio) describes formulations of peptides and polypeptides including insulin which contain an alkylglycoside, which component is said to reduce aggregation and immunogenicity.

WO2012/006283 (Pohl) describes formulations containing insulin together with a zinc chelator such as ethylenediaminetetraacetate (EDTA). Modulating the type and quantity of EDTA is said to change the insulin absorption profile. Calcium EDTA is the preferred form of EDTA since it is said to be associated with reduced pain at the injection site and is less likely to remove calcium from the body. Preferred formulations also contain citrate which is said to further enhance absorption and to improve the chemical stability of the formulation.

US2010/0227795 (Steiner) describes a composition comprising insulin, a dissociating agent such as citric acid or sodium citrate, and a zinc chelator such as EDTA wherein the formulation has a physiological pH and is a clear aqueous solution. The formulations are said to have improved stability and rapid onset of action.

WO2015/120457 (Wilson) describes stabilized ultra-rapid acting insulin formulations comprising insulin in combination with a zinc chelator such as EDTA, a dissolution/stabilization agent such as citric acid, a magnesium salt, a zinc compound and optionally additional excipients.

Further approaches to accelerating the absorption and effect of insulin through the use of specific accelerating additives have been described:

WO91/09617 (Jorgensen) reports that nicotinamide or nicotinic acid or a salt thereof increases the speed of absorption of insulin from aqueous preparations administered parenterally.

WO2010/149772 (Olsen) describes a formulation comprising insulin, a nicotinic compound and arginine. The presence of arginine is said to improve the chemical stability of the formulation.

WO2015/1171484 (Christe) described rapid acting formulations of insulin wherein onset of action and/or absorption of insulin is faster due to the presence of treprostinil.

US2013/0231281 (Soula) describes an aqueous solution composition comprising insulin or an insulin analogue and at least one oligosaccharide whose average degree of polymerisation is between 3 and 13 and whose polydispersity index is above 1.0, said oligosaccharide having partially substituted carboxyl functional groups, the unsubstituted carboxyl functional groups being salifiable. Such a formulation is said to be rapid acting.

It would be desirable if analogues or formulations of insulin were available which were ultra rapid acting, thus, more closely matching the activity of physiological insulin. There also remains a need in the art to provide further, and preferably improved, formulations of insulin and insulin analogues which are rapid acting and stable.

SUMMARY OF THE INVENTION

According to the invention there is provided an aqueous liquid pharmaceutical formulation comprising insulin or an insulin analogue, ionic zinc, a chelating agent and polysorbate 80 ("the formulation of the invention").

The formulation of the invention may be used in treatment of subjects suffering from diabetes mellitus, particularly Type 1 diabetes mellitus especially for administration at meal times.

As can be seen from the accompanying examples, formulations of the invention are significantly more stable than corresponding formulations without polysorbate 80 or corresponding formulations in which polysorbate 80 is substituted by another non-ionic surfactant. The formulations are expected to be more rapidly acting than corresponding formulations which do not contain a chelating agent.

Description of the sequence listing:
SEQ ID NO: 1: A chain of human insulin
SEQ ID NO: 2: B chain of human insulin
SEQ ID NO: 3: B chain of insulin lispro
SEQ ID NO: 4: B chain of insulin aspart
SEQ ID NO: 5: B chain of insulin glulisine

DETAILED DESCRIPTION OF THE INVENTION

As used herein, "insulin" refers to native human insulin having an A chain and a B chain as set out in SEQ ID NOs. 1 and 2 and containing and connected by disulfide bridges as in the native molecule (Cys A6-Cys A11, Cys B7 to Cys A7 and Cys-B19-Cys A20). Insulin is suitably recombinant insulin.

"Insulin analogue" refers to an analogue of insulin which is an insulin receptor agonist and has a modified amino acid sequence, such as containing 1 or 2 amino acid changes in the sequence of the A or B chain (especially the B chain). Exemplary insulin analogues include faster acting analogues such as insulin lispro, insulin aspart and insulin glulisine. These forms of insulin have the human insulin A chain but variant B chains—see SEQ ID NOs. 3-5. Further faster acting analogues are described in EP0214826, EP0375437 and EP0678522 the contents of which are herein incorporated by reference in their entirety.

In one embodiment the insulin or insulin analogue is recombinant human insulin. In another embodiment it is insulin lispro. In another embodiment it is insulin aspart. In another embodiment it is insulin glulisine.

The term "aqueous pharmaceutical formulation", as used herein, refers to a formulation suitable for therapeutic use in which the aqueous component is or comprises water, preferably distilled water, deionized water, water for injection, sterile water for injection or bacteriostatic water for injection. The aqueous pharmaceutical formulations of the invention are solution formulations in which all components are dissolved in water.

The concentration of insulin or insulin analogue in the formulation will typically be in the range 10-1000 U/ml, such as 50-500 U/ml e.g. 50-200 U/ml. An exemplary formulation contains insulin or insulin analogue at a concentration of 100 U/ml (around 3.6 mg/ml). Another range of interest is 500-1000 U/ml e.g. 800-1000 U/ml and another exemplary formulation contains insulin or insulin analogue at a concentration of 1000 U/ml (around 36 mg/ml).

The formulations of the invention contain ionic zinc i.e. $Zn^{2+}$ ions. The source of the ionic zinc will typically be a water soluble zinc salt such as $ZnCl_2$, $ZnO$, $ZnSO_4$, $Zn(NO_3)_2$ or $Zn(acetate)_2$ and most suitably $ZnCl_2$ or $ZnO$.

The concentration of the ionic zinc in the formulation will typically be more than 0.05% e.g. more than 0.1% e.g. more than 0.2% e.g. more than 0.25% by weight of zinc based on the weight of insulin or insulin analogue in the formulation, for example 0.25-1%, e.g. 0.35-0.75%, e.g. 0.45-0.6% by weight of zinc based on the weight of insulin or insulin analogue in the formulation. For the purpose of the calculation the weight of counter ion to zinc is excluded. The concentration of the ionic zinc in the formulation will (for example, for a formulation containing 100 U/ml of insulin or insulin analogue) typically be more than 0.015 mM e.g. more than 0.03 mM e.g. more than 0.06 mM, more than 0.09 mM or more than 0.12 mM. Thus, the concentration of the ionic zinc in the formulation will typically be more than 0.15 mM, for example 0.15-0.60 mM, e.g. 0.20-0.45 mM, e.g. 0.25-0.35 mM.

In a formulation e.g. containing 1000 U/ml of insulin or insulin analogue the concentration of the ionic zinc will typically be more than 0.15 mM e.g. more than 0.3 mM e.g. more than 0.6 mM, more than 0.9 mM or more than 1.2 mM. Thus, the concentration of the ionic zinc in the formulation may be more than 1.5 mM, for example 1.5-6.0 mM, e.g. 2.0-4.5 mM, e.g. 2.5-3.5 mM.

The formulations of the invention contain a chelating agent. Chelating agents should be capable of complexing ionic zinc and typically will have a log K metal binding stability constant with respect to zinc binding of at least 4.5 as determined at 25° C. Metal binding stability constants listed in the National Institute of Standards and Technology reference database 46 (Critically Selected Stability Constants of Metal Complexes) can be used. The database typically lists log K constants determined at 25° C. Therefore, the suitability of a chelating agent for the present invention can be determined based on its log K metal binding stability constant with respect to zinc binding, as measured at 25° C. and as quoted by the database. Exemplary chelating agents include polydendate organic anions. A preferred chelating agent is EDTA (log K=14.5). Further examples include citrate (log K=4.93), EGTA (log K=12.6), pyrophosphate (log K=8.71) and alginate (log K=6.91). A further preferred chelating agent is citrate. Other possible chelating agents include substances that can contribute a lone pair of electrons or electron density for interaction with ionic zinc such as polydentate amines including ethylenediamine and aromatic or heteroaromatic substances especially those comprising an imidazole moiety such as histidine (log K=6.51).

The most suitable concentration of the chelating agent will depend on the agent and its log K value and will typically be in the range 0.1-100 mM e.g. 0.1-50 mM.

For example, the concentration of the chelating agent in the formulation may typically be in the range 0.1-2 mM, e.g. 0.2-1 mM, e.g. 0.3-1 mM, more preferably 0.3-0.5 mM, more preferably around 0.4 mM, especially when the chelating agent is EDTA. For example, the concentration of the chelating agent in the formulation in the formulation may typically be in the range 2.5-50 mM, e.g. 5-50 mM, more preferably 5-30 mM, more preferably around 20 mM (e.g. 22 mM), especially when the chelating agent is citrate or histidine and especially for insulin or insulin analogue 100 U/ml formulations. Suitably the concentration of the zinc binding species in the formulation is 10-50 mM e.g. 30-50 mM e.g. 40-50 mM, more preferably around 44 mM when the zinc binding species is citrate or histidine for insulin or insulin analogue 1000 U/ml formulations.

Chelating agents such as EDTA, citrate, EGTA, pyrophosphate or alginate may be employed as the free acid or a salt form, such as a salt form with sodium or calcium ions, especially sodium ions.

Chelating agents which have acid forms (e.g. citric acid) may be introduced into the aqueous formulations of the invention in the form of a salt of the acid, such as a sodium salt (e.g. sodium citrate). Alternatively, they can be introduced in the form of the acid with subsequent adjustment of pH to the required level.

A mixture of chelating agents may be employed, although a single chelating agent is preferred.

Suitably the molar ratio of ionic zinc to chelating agent in the formulation is in the range 1.0:0.8 to 1:500 e.g. 1.0:0.8 to 1:100.

For example, a suitable range of ionic zinc to chelating agent is 1.0:0.8 to 1.0:2.0, e.g. 1.0:0.95 to 1.0:1.5, e.g. 1.0:1.0 to 1.0:1.4, especially for EDTA as chelating agent. The suitable molar ratio can be adapted accordingly for chelating agents with lower log K dissociation constants than EDTA with respect to Zn binding. For example, another suitable molar ratio of ionic zinc to chelating agent is 1:20-1:100, e.g. 1:40-1:90, e.g. 1:60-1:80, especially for citrate or histidine as chelating agent.

For example, a formulation containing 100 U/ml of insulin or insulin analogue may contain around 0.3 mM of ionic zinc (i.e. around 19.5 µg/ml of ionic zinc, i.e. around 0.54% by weight of zinc based on the weight of insulin or insulin analogue in the formulation) and around 0.3-0.4 mM chelating agent (especially EDTA).

For example, a formulation containing 100 U/ml of insulin or insulin analogue may contain around 0.3 mM of ionic zinc (i.e. around 19.5 µg/ml of ionic zinc, i.e. around 0.54% by weight of zinc based on the weight of insulin or insulin analogue in the formulation) and around 20 mM (e.g. 22 mM) chelating agent (especially citrate).

The formulations of the invention contain polysorbate 80 (also known as polyoxyethylene (20) sorbitan monooleate) which is a non-ionic surfactant. Thus, polysorbate 80 is a mono ester formed from oleic acid and polyoxyethylene (20) sorbitan in which the number 20 indicates the number of oxyethylene groups in the molecule. Polysorbate 80 is known under a range of brand names including in particular Tween 80, and also Alkest TW 80.

The concentration of the polysorbate 80 in the formulation will typically be in the range 1-800 µg/ml, e.g. 1-500 µg/ml, e.g. 5-200 µg/ml, such as 5-50 µg/ml especially around 20 µg/ml. For higher concentrations of insulin compound e.g. 500-1000 U/ml a higher concentration of polysorbate 80 may be suitable e.g. 300-600 µg/ml, such as 400-500 µg/ml especially around 500 µg/ml.

Suitably the pH of the aqueous formulations of the invention is in the range 5.5-9.0 especially 6.5-8.0 e.g. 7.0-7.5. In order to minimise injection pain the pH is preferably close to physiological pH (around pH 7.4). Another pH range of interest is 7.6-8.0 e.g. around 7.8.

Suitably, the composition of the invention comprises a buffer in order to stabilise the pH of the formulation, which can also be selected to enhance protein stability. In one embodiment, a buffer is selected to have a pKa close to the pH of the composition; for example histidine is suitably employed as a buffer when the pH of the composition is in the range 5.0-7.0. Such a buffer may be employed in a concentration of 0.5-5 mM e.g. 1-2 mM. If histidine is included in the formulation as a chelating agent it will also have a buffering role at this pH. If citrate is included in the formulation as a chelating agent it may also have a buffering role. As another example, phosphate is suitably employed as a buffer when the pH of the composition is in the range 6.1-8.1. Such a buffer may be employed in a concentration of 0.5-3 mM e.g. 0.5-2 mM. Alternatively, in another embodiment, the formulation of the invention is further stabilised as disclosed in WO2008/084237 (herein incorporated by reference in its entirety), which describes a formulation comprising a protein and one or more additives, characterised in that the system is substantially free of a conventional buffer, i.e. a compound with an ionisable group having a pKa within 1 unit of the pH of the formulation at the intended temperature range of storage of the composition, such as 25° C. In this embodiment, the pH of the formulation is set to a value at which the formulation has maximum measurable stability with respect to pH; the one or more additives (displaced buffers) are capable of exchanging protons with the insulin or insulin analogue and have pKa values at least 1 unit more or less than the pH of the formulation at the intended temperature range of storage of the formulation. The additives may have ionisable groups having pKa between 1 to 5 pH units, preferably between 1 to 3 pH units, most preferably from 1.5 to 2.5 pH units, of the pH of the aqueous formulation at the intended temperature range of storage of the composition (e.g. 25° C.). Such additives may typically be employed at a concentration of 0.5-10 mM e.g. 2-5 mM.

The ionic strength of a formulation may be calculated according to the formula $$I = 0.5 \times \sum_{X=1}^{n} c_x z_x^2$$

in which $c_x$ is molar concentration of ion x (mol L$^{-1}$), $z_x$ is the absolute value of the charge of ion x and the sum covers all ions (n) present in the composition. The contribution of the insulin or insulin analogue itself should be ignored for the purposes of the calculation. For zwitterions the absolute value of the charge is the total charge excluding polarity, e.g. for glycine the possible ions have absolute charge of 0, 1 or 2 and for aspartate the possible ions have absolute charge of 0, 1, 2 or 3. The ionic strength of the formulation is suitably kept to a minimum level since higher ionic strength formulations are less stable than lower ionic strength formulations.

In general, the ionic strength of the formulation is suitably in the range of around 1 mM up to around 500 mM.

Suitably the ionic strength is less than 40 mM, e.g. less than 20 mM, e.g. less than 10 mM.

When the insulin analogue is insulin lispro, the ionic strength of the formulation is suitably kept to a minimum level since higher ionic strength formulations are less stable than lower ionic strength formulations. Suitably the ionic strength taking account of ions in the formulation except for the zinc binding species and the insulin analogue is less than 40 mM, e.g. less than 20 mM, e.g. less than 10 mM such as 1-10 mM.

When the insulin analogue is insulin aspart at a concentration of >500 U/ml (e.g. 1000 U/ml), the ionic strength of the formulation is suitably kept to a minimum level since higher ionic strength formulations are less stable than lower ionic strength formulations. Suitably the ionic strength taking account of ions in the formulation except for the zinc binding species and the insulin analogue is less than 40 mM, e.g. less than 20 mM, e.g. less than 10 mM.

When the insulin analogue is insulin aspart at a concentration of 500 U/ml or less (e.g. 100 U/ml), the ionic strength of the formulation may be high. Suitably the ionic strength taking account of ions in the formulation except for the zinc binding species and the insulin analogue is more than 50 mM, e.g. more than 100 mM, e.g. 50-500 mM or 100-500 mM or 100-300 mM such as around 150 mM.

The aqueous formulations of the present invention cover a wide range of osmolarity, including hypotonic, isotonic and hypertonic compositions. Preferably, the formulations of the invention are substantially isotonic. Suitably the osmolarity of the formulation is selected to minimize pain according to the route of administration e.g. upon injection. Preferred formulations have an osmolarity in the range of about 200 to about 500 mOsm/L. Preferably, the osmolarity is in the range of about 250 to about 350 mOsm/L. More preferably, the osmolarity is about 300 mOsm/L.

Tonicity of the formulation may be adjusted with a tonicity modifying agent. Tonicity modifying agents may be charged or uncharged and uncharged tonicity modifying agents are preferred. Examples of charged tonicity modifying agents include salts such as a combination of sodium, potassium, magnesium or calcium ions, with chloride, sulfate, carbonate, sulfite, nitrate, lactate, succinate, acetate or maleate ions (especially sodium chloride or sodium sulphate, particularly sodium chloride). Amino acids such as arginine, glycine or histidine may also be used for this purpose. Examples of uncharged tonicity modifying agents include sugars, sugar alcohols and other polyols, such as trehalose, sucrose, mannitol, glycerol, 1,2-propanediol, raffinose, lactose, dextrose, sorbitol or lactitol (especially trehalose, mannitol, glycerol or 1,2-propanediol, particularly glycerol).

The formulations of the invention can optionally include preservative, preferably phenol, m-cresol, chlorocresol, benzyl alcohol, propylparaben, methylparaben, benzalkonium chloride or benzethonium chloride.

The formulations of the invention may optionally comprise nicotinamide. The presence of nicotinamide may further increase the speed of onset of action of insulin formulated in compositions of the invention. Suitably, the concentration of nicotinamide is in the range 10-150 mM, preferably in the range 20-100 mM, such as around 80 mM.

The formulations of the invention may optionally comprise nicotinic acid or a salt thereof. The presence of nicotinic acid or a salt thereof may also further increase the speed of onset of action of insulin formulated in compositions of the invention. Suitably, the concentration of nicotinic acid or a salt thereof is in the range 10-150 mM, preferably in the range 20-100 mM, such as around 80 mM. Example salts include metal salts such as sodium, potassium and magnesium salts.

Typically one of nicotinamide and nicotinic acid (or as salt thereof) may be included in the formulation but not both.

Formulations of the invention may optionally include other beneficial components including stabilising agents. For example amino acids such as arginine and proline may be included which may have stabilising properties.

In an embodiment of the invention the formulations are free of acids selected from glutamic acid, ascorbic acid, succinic acid, aspartic acid, maleic acid, fumaric acid, adipic acid and acetic acid and are also free from the corresponding ionic forms of these acids. In an embodiment of the invention the formulations are free of citric acid and are also free from the corresponding ionic forms of this acid.

In an embodiment of the invention the formulations are free of protamine and protamine salts.

In an embodiment of the invention the formulations are free of magnesium ions.

In an embodiment of the invention the formulations are free of calcium ions.

Suitably the formulations of the invention are sufficiently stable that the concentration of high molecular weight species remains low upon extended storage. The term "high molecular weight species" as used herein, refers to any irreversibly formed component of the protein content which has an apparent molecular weight at least about double the molecular weight of the parent insulin or insulin analogue, as detected by a suitable analytical method, such as size-exclusion chromatography. That is, high molecular weight species are multimeric aggregates of the parent insulin or insulin analogue. The multimeric aggregates may comprise the parent protein molecules with considerably altered conformation or they may be an assembly of the parent protein units in the native or near-native conformation. The determination of high molecular weight species can be done using methods known in the art, including size exclusion chromatography, electrophoresis, analytical ultracentrifugation, light scattering, dynamic light scattering, static light scattering and field flow fractionation.

Suitably the formulations of the invention are sufficiently stable that they remain substantially free of visible particles after storage at 30° C. for at least one, two or three months.

Visible particles are suitably detected using the 2.9.20. European Pharmacepoeia Monograph (Particulate Contamination: Visible Particles)

Suitably the formulations of the invention are sufficiently stable that the concentration of related species remains low upon extended storage. The term "related species" as used herein, refers to any component of the protein content formed by a chemical modification of the parent insulin or insulin analogue, particularly desamido or cyclic imide forms of insulin. Related species are suitably detected by RP-HPLC.

In a preferred embodiment, the formulation of the invention retains at least 95%, e.g. at least 96%, e.g. at least 97%, e.g. at least 98% native insulin or native insulin analogue (by weight of total protein) after storage at 30° C. for at least one, two or three months. The percentage of insulin or insulin analogue (by weight of total protein) may be determined by size-exclusion chromatography or RP-HPLC.

In a preferred embodiment, the formulation of the invention comprises no more than 4% (by weight of total protein), preferably no more than 2% high molecular weight species after storage at 30° C. for at least one, two or three months.

In a preferred embodiment, the formulation of the invention comprises no more than 4% (by weight of total protein), preferably no more than 2% A-21 desamido form of the insulin or the insulin analogue after storage at 30° C. for at least one, two or three months.

In preferred embodiments, a composition of the present invention should exhibit an increase in high molecular weight species during storage which is at least 10%, lower, preferably at least 25% lower, more preferably at least 50% lower, than a composition lacking the polysorbate 80 but otherwise identical, following storage under the same conditions and length of time.

In preferred embodiments, a composition of the present invention should exhibit an increase in related species during storage which is at least 10% lower, preferably at least 25% lower, more preferably at least 50% lower, than a composition lacking the polysorbate 80 but otherwise identical, following storage under the same conditions and length of time.

The speed of action of a formulation of the invention may be determined in the Diabetic Pig Pharmacokinetic/Pharmacodynamic Model (see Examples, General Methods). In preferred embodiments, a composition of the present invention should exhibit a $T_{max}$ (i.e. time to peak insulin concentration) that is least 10% shorter, preferably at least 20% shorter, more preferably at least 30% shorter than a composition lacking the chelating agent but otherwise identical, using the model. In preferred embodiments, a composition of the present invention should exhibit an area under the curve on the pharmacodynamics profile within the first 45 minutes after injection that is least 10% greater, preferably at least 20% greater, more preferably at least 30% greater than a composition lacking the chelating agent but otherwise identical, using the model.

According to further aspects of the invention, there is provided a formulation of the invention for use in the treatment of a subject suffering from diabetes mellitus. There is also provided a method of treatment of diabetes mellitus which comprises administering to a subject in need thereof an effective amount of a formulation of the invention.

A typical dose of the composition of the invention is 2-30 U, e.g. 5-15 U. Administration should suitably occur in the window between 15 minutes before eating (i.e. before start of a meal) and 15 minutes after eating (i.e. after end of a meal).

An aspect of the invention is a container e.g. made of plastics or glass containing one dose or a plurality of doses of the formulation of the invention. The container can, for example, be a cartridge designed to be a replaceable item for use with an injection device.

The formulations of the invention may suitably be packaged for injection, especially sub-cutaneous or intramuscular injection. Sub-cutaneous injection is preferred. Injection may be by conventional syringe or more preferably via a pen device adapted for use by diabetic subjects. Exemplary pen devices include the Kwikpen® device and the Flexpen® device.

An aspect of the invention is an injection device, particularly a device adapted for subcutaneous or intramuscular injection, for single or multiple use comprising a container containing one dose or a plurality of doses of the formulation of the invention together with an injection needle. In an embodiment the container is a replaceable cartridge which contains a plurality of doses. In an embodiment, the needle is replaceable e.g. after each occasion of use.

Another aspect of the invention is a medical device comprising a reservoir comprising plurality of doses of the formulation of the invention and a pump adapted for automatic or remote operation such that upon automatic or remote operation one or more doses of the formulation of the invention is administered to the body e.g. subcutaneously or intramuscularly. Such devices may be worn on the outside of the body or implanted in the body.

Formulations of the invention may be prepared by mixing the ingredients. For example, the insulin or insulin analogue may be dissolved in an aqueous formulation comprising the other components. Alternatively, the insulin or insulin analogue may be dissolved in a strong acid (typically HCl), after dissolution diluted with an aqueous formulation comprising the other components, and then pH adjusted to the desired pH with addition of alkali (e.g. NaOH). As a variation on this method, a step of neutralising the acid solution may be performed before the dilution step and it may then not be necessary to adjust the pH after the dilution step (or a small adjustment only may be necessary).

According to another aspect of the invention there is provided a dry solid pharmaceutical composition suitable for reconstitution with an aqueous medium which comprises insulin or an insulin analogue, ionic zinc, a chelating agent and polysorbate 80. Thus, a formulation of the invention may be prepared by dissolving such a dry solid pharmaceutical composition in an aqueous medium e.g. water or saline. Such a dry solid pharmaceutical composition may be prepared by dehydrating (e.g. freeze drying) a formulation of the invention. The invention also provides a container containing one dose or a plurality of doses of such a dry solid pharmaceutical composition.

The invention includes an aqueous liquid pharmaceutical formulation comprising insulin or an insulin analogue, ionic zinc, a chelating agent and polysorbate 80. In some embodiments, the formulation comprises insulin lispro as an insulin analogue. In some embodiments, the formulation comprises insulin aspart as an insulin analogue. In some embodiments, the formulation comprises insulin glulisine as an insulin analogue. In some embodiments, the formulation comprises recombinant human insulin as an insulin. In additional embodiments, the insulin or insulin analogue is present in the formulation at a concentration of 10-1000 U/ml. In additional embodiments, the ionic zinc in the formulation is present at a concentration of more than 0.05% e.g. more than 0.25% by weight of zinc based on the weight of insulin or insulin analogue in the formulation. In further embodiments, the ionic zinc is present at a concentration of 0.25-1% by weight of zinc based on the weight of insulin or insulin analogue in the formulation. In additional embodiments, the chelating agent in the formulation has a metal binding stability constant log K with respect to zinc binding of at least 4.5 as determined at 25° C. In some embodiments, the chelating agent is EDTA. In some embodiments, the chelating agent is selected from citrate, EGTA, pyrophosphate, alginate, ethylenediamine and histidine. In other embodiments, the chelating agent is citrate. In further embodiments, the source of the citrate of the chelating agent in the formulation is citric acid. In other embodiments, the chelating agent is histidine. In some embodiments, the chelating agent is present in the formulation at a concentration of 0.1-50 mM. In some embodiments, the chelating agent in the formulation is EDTA at a concentration of 0.1-2 mM. In some embodiments, the chelating agent in the formulation is citrate at a concentration of 2.5-50 mM. In additional embodiments, the molar ratio of ionic zinc to EDTA as chelating agent in the formulation is in the range 1:0.8 to 1.0:2.0. In additional embodiments, the molar ratio of ionic zinc to citrate as chelating agent is in the range 1:20-1:100. In additional embodiments, the polysorbate 80 in the formulation of the invention is present at a concentration of 1-500 µg/ml. In additional embodiments, the formulation further comprises an uncharged tonicity modifier. In some embodiments, the uncharged tonicity modifier is selected from the group consisting of trehalose, mannitol, glycerol or 1,2-propanediol. In some embodiments, the uncharged tonicity modifier is glycerol. In additional embodiments, the formulation is isotonic. In additional embodiments, the pH of the formulation is in the range 5.5 to 9.0. In some embodiments, the pH is in the range 7.0 to 7.5. In further embodiments, the pH is in the range 7.6 to 8.0. In additional embodiments, the formulation, further comprises a preservative. In some embodiments, the preservative is selected from the group consisting of phenol, m-cresol, chlorocresol, benzyl alcohol, propylparaben, methylparaben, benzalkonium chloride and benzethonium chloride. In additional embodiments, the ionic strength of the formulation is less than 40 mM. In additional embodiments, the formulation is for use in the treatment of a subject suffering from diabetes mellitus. In some embodiments, the disclosure provides a method of treatment of diabetes mellitus which comprises administering to a subject in need thereof an effective amount of a formulation of the invention. In some embodiments, the disclosure provides a container containing one dose or a plurality of doses of the formulation. In an additional embodiment, the invention provides an injection device for single or multiple use comprising a container containing one dose or a plurality of doses of the formulation of the invention together with an injection needle. In some embodiments, the invention provides a medical device comprising a reservoir comprising plurality of doses of the formulation and a pump adapted for automatic or remote operation such that upon automatic or remote operation one or more doses of the formulation is administered to the body. In an additional embodiment, the invention provides a dry solid pharmaceutical composition suitable for reconstitution with an aqueous medium which comprises insulin or an insulin analogue, ionic zinc, a chelating agent and polysorbate 80. In one embodiment, the invention provides a method of preparing a formulation of the invention which comprises dissolving a dry solid pharmaceutical composition of the invention in an aqueous medium. In another embodiment, the invention provides a method of improving the storage stability of an aqueous liquid pharmaceutical formulation comprising insulin or an insulin analogue, ionic zinc and a chelating agent which comprises adding polysorbate 80 to the formulation. In an additional embodiment, the invention provides the use of polysorbate 80 to improve the storage stability of an aqueous liquid pharmaceutical formulation comprising insulin or an insulin analogue, ionic zinc and a chelating agent.

Further aspects of the invention include:

[A] An aqueous liquid pharmaceutical formulation comprising (i) an insulin or an insulin analogue, (ii) ionic zinc, (iii) a chelating agent at a concentration of 0.1-100 mM e.g. 0.1-50 mM, and (iv) polysorbate 80 at a concentration of 1-800 µg/ml, e.g. 1-500 µg/ml, e.g. 5-200 µg/ml, e.g. 5-50 µg/ml, e.g. 20 µg/ml. In some embodiments, the chelating agent is selected from citrate, EGTA, pyrophosphate, alginate, ethylenediamine and histidine. In some embodiments, the chelating agent is citrate e.g. at a concentration of 2.5-50 mM, e.g. 5-50 mM, e.g. 5-30 mM e.g. 22 mM or 10-50 mM e.g. 30-50 mM e.g. 44 mM. In some embodiments, the chelating agent is histidine e.g. at a concentration of 2.5-50 mM, e.g. 5-50 mM, e.g. 5-30 mM, e.g. 22 mM, or 10-50 mM, e.g. 30-50 mM, e.g. 44 mM. In some embodiments, the chelating agent is EDTA e.g. at a concentration of 0.1-2 mM, e.g. 0.2-1 mM, e.g. 0.3-1 mM, e.g. 0.3-0.5 mM, e.g. 0.4 mM. In some embodiments, the ionic zinc is present at a concentration of more than 0.05% e.g. more than 0.1% e.g. more than 0.2% e.g. 0.25-1% e.g. 0.35-0.75% e.g. 0.45-0.6% by weight of zinc based on the weight of insulin or insulin analogue in the formulation. In some embodiments, the ionic zinc is present at a concentration of more than 0.015 mM, e.g. more than 0.15 mM, e.g. 0.15-0.60 mM, e.g. 0.20-0.45 mM, e.g. 0.25-0.35 mM. In some embodiments, the ionic zinc is present at a concentration of more than 1.5 mM, e.g. 1.5-6.0 mM, e.g. 2.0-4.5, e.g. 2.5-3.5 mM. In some embodiments, the insulin or insulin analogue is present at a concentration of 10-1000 U/ml, e.g., 50-500 U/ml, 50-200 U/ml e.g. 100 U/ml. In some embodiments, the insulin or insulin analogue is present at a concentration of 500-1000 U/ml, e.g. 800-1000 U/ml, e.g. 1000 U/ml. In a first further embodiment, the formulation comprises the insulin analogue insulin lispro. In a second further embodiment, the formulation comprises the insulin analogue insulin aspart. In a third further embodiment, the formulation comprises the insulin analogue insulin glulisine. In a fourth further embodiment, the formulation comprises recombinant human insulin.

[B] The aqueous liquid pharmaceutical formulation of [A], further comprising one or more buffers e.g. phosphate such as sodium phosphate.

[C] The aqueous liquid pharmaceutical formulation of [A] or [B], further comprising one or more preservatives e.g. phenol, m-cresol, chlorocresol, benzyl alcohol, propylparaben, methylparaben, benzalkonium chloride or benzethonium chloride.

[D] The aqueous liquid pharmaceutical formulation of [A], [B], or [C], further comprising one or more tonicity modifiers e.g. glycerol or NaCl.

[E] The aqueous liquid pharmaceutical formulation of [A], [B], [C] or [D], further comprising nicotinamide, nicotinic acid or a salt thereof. In one embodiment, the nicotinamide, nicotinic acid or salt thereof, is at a concentration in the range of 10-150 mM, preferably in the range 20-100 mM, such as around 80 mM.

[F] The aqueous liquid pharmaceutical formulation of [A], [B], [C], [D] or [E], wherein the ionic strength of the formulation is less than 40 mM.

[G] A method of improving the storage stability of an aqueous liquid pharmaceutical formulation comprising insulin or an insulin analogue, ionic zinc and a chelating agent which comprises adding polysorbate 80 to the formulation.

[H] Use of polysorbate 80 to improve the storage stability of an aqueous liquid pharmaceutical formulation comprising insulin or an insulin analogue, ionic zinc and a chelating agent.

Aspects of the invention, without limitation, are defined by the following embodiments:

[1] An aqueous liquid pharmaceutical formulation comprising insulin or an insulin analogue, ionic zinc, a chelating agent and polysorbate 80.

[2] The formulation according to embodiment [1] comprising insulin lispro as an insulin analogue.

[3] The formulation according to embodiment [1] comprising insulin aspart as an insulin analogue.

[4] The formulation according to embodiment [1] comprising insulin glulisine as an insulin analogue.

[5] The formulation according to embodiment [1] comprising recombinant human insulin as an insulin.

[6] The formulation according to any one of embodiments [1] to [5], wherein the insulin or insulin analogue is present at a concentration of 10-1000 U/ml.

[7] The formulation according to any one of embodiments [1] to [6], wherein the ionic zinc is present at a concentration of more than 0.25% by weight of zinc based on the weight of insulin or insulin analogue in the formulation.

[8] The formulation according to embodiment [7], wherein the ionic zinc is present at a concentration of 0.25-1% by weight of zinc based on the weight of insulin or insulin analogue in the formulation.

[9] The formulation according to any one of embodiments [1] to [8], wherein the chelating agent has a metal binding stability constant log K with respect to zinc binding of at least 4.5 at 25° C.

[10] The formulation according to any one of embodiments [1] to [9], wherein the chelating agent is EDTA.

[11] The formulation according to any one of embodiments [1] to [9], wherein the chelating agent is selected from citrate, EGTA, pyrophosphate, alginate, ethylenediamine and histidine.

[12] The formulation according to embodiment [11], wherein the chelating agent is citrate.

[13] The formulation according to embodiment [12] wherein the source of the citrate is citric acid.

[14] The formulation according to any of embodiments [1] to [13], wherein the chelating agent is present at a concentration of 0.1-50 mM.

[15] The formulation according to embodiment [10] wherein EDTA as chelating agent is present at a concentration of 0.1-2 mM.

[16] The formulation according to embodiment [12] or [13] wherein citrate as chelating agent are present at a concentration of 2.5-50 mM.

[17] The formulation according to any one of embodiments [10], [14] or [15] wherein the molar ratio of ionic zinc to EDTA as chelating agent is in the range 1:0.8 to 1.0:2.0.

[18] The formulation according to any one of embodiments [11] to [14] or [16], wherein the molar ratio of ionic zinc to citrate as chelating agent is in the range 1:20-1:100.

[19] The formulation according to any one of embodiments [1] to [18], wherein the polysorbate 80 is present at a concentration of 1-500 µg/ml.

[20] The formulation according to any one of embodiments [1] to [19], further comprising an uncharged tonicity modifier.

[21]] The formulation according to embodiment [20], wherein the uncharged tonicity modifier is selected from the group consisting of trehalose, mannitol, glycerol or 1,2-propanediol.

[22] The formulation according to embodiment [21], wherein the uncharged tonicity modifier is glycerol.

[23] The formulation according to any one of embodiments [1] to [22], wherein the composition is isotonic.

[24] The formulation according to any one of embodiments [1] to [23], wherein the pH is in the range [5]5 to [90.

[25] The formulation according to embodiment [24], wherein the pH is in the range 7.0 to 7.5.

[26] The formulation according to embodiment [24], wherein the pH is in the range 7.6 to 8.0.

[27] The formulation according to any of embodiments [1] to [26], further comprising a preservative.

[28] The formulation according to embodiment [27], wherein the preservative is selected from the group consisting of phenol, m-cresol, chlorocresol, benzyl alcohol, propylparaben, methylparaben, benzalkonium chloride and benzethonium chloride.

[29] The formulation according to any one of embodiments [1] to [28] wherein the ionic strength of the formulation is less than 40 mM.

[30] A formulation according to any one of embodiments [1] to [29] for use in the treatment of a subject suffering from diabetes mellitus.

[31] A method of treatment of diabetes mellitus which comprises administering to a subject in need thereof an effective amount of a formulation according to any one of embodiments [1] to [29].

[32] A container containing one dose or a plurality of doses of the formulation according to any one of embodiments [1] to [29].

[33] An injection device for single or multiple use comprising a container containing one dose or a plurality of doses of the formulation according to any one of embodiments [1] to [29] together with an injection needle.

[34] A medical device comprising a reservoir comprising plurality of doses of the formulation according to any one of embodiments [1] to [29] and a pump adapted for automatic or remote operation such that upon automatic or remote operation one or more doses of the formulation is administered to the body.

[35] A dry solid pharmaceutical composition suitable for reconstitution with an aqueous medium which comprises insulin or an insulin analogue, ionic zinc, a chelating agent and polysorbate 80.

[36] A method of preparing a formulation according to any one of embodiments [1] to [29] which comprises dissolving a dry solid pharmaceutical composition according to embodiment [35] in an aqueous medium.

[37] A method of improving the storage stability of an aqueous liquid pharmaceutical formulation comprising insulin or an insulin analogue, ionic zinc and a chelating agent which comprises adding polysorbate 80 to the formulation.

[38] Use of polysorbate 80 to improve the storage stability of an aqueous liquid pharmaceutical formulation comprising insulin or an insulin analogue, ionic zinc and a chelating agent.

Formulations of the invention are expected to have one or more of the following advantageous properties:
- rapid speed of action, typically faster than normal human insulin, upon administration to a subject;
- good physical stability upon storage, especially as measured by the amount of HMWS or visual detection of particles;
- good chemical stability upon storage, especially as measured by the amount of related products e.g. products of deamidation.

EXAMPLES

General Methods
Size Exclusion Chromatography

Ultra-high performance size exclusion chromatography of insulin preparations was performed using the Waters ACQUITY H-class Bio UPLC® system with a 1.7 µm Ethylene Bridged Hybrid 125 Å pore packing material in a 300 mm by 4.6 mm column. The column was equilibrated in 0.65 mg/ml L-arginine, 20% v/v acetonitrile, 15% v/v glacial acetic acid mobile phase and 10 µl of sample, acidified with 0.01M HCl, was analysed at 0.4 mL/min, with 276 nm UV detection. All analyses were performed at ambient temperature.

Reversed-Phase

Ultra-high performance reverse phase chromatography was performed using the Waters ACQUITY H-class Bio UPLC® system with a 1.7 µm Ethylene Bridged Hybrid particle, 130 Å pore resin trifunctionally immobilised with a C18 ligand in a 50 mm by 2.1 mm column. Insulin samples were bound in an 82% w/v $Na_2SO_4$, 18% v/v acetonitrile, pH 2.3 mobile phase and eluted in 50% w/v $Na_2SO_4$, 50% v/v acetonitrile gradient flow. 2 µl of sample was acidified with 0.01M HCl and analysed at 0.61 mL/min, with 214 nm UV detection. All analyses were performed at 40° C.

The Diabetic Pig Pharmacokinetic/Pharmacodynamic Model: Method for Determining Speed of Action:

10-15 male diabetic Yucatan miniature pigs are used. Pigs are injected subcutaneously with a sample of the test formulation and blood is taken (1 or 2 ml) at the following time-points (min) with respect to the injection: +30 (or −15), 0, 5, 10, 15, 30, 45, 60, 75, 90, 105, 120, 150, 180, 240, 360. For pharmacodynamics profile, serum is analysed for glucose (using a commercially available glucometer). For pharmacokinetic profile, insulin concentration is determined in the serum using an immunoassay.

Visual Assessment

Visible particles are suitably detected using the 2.9.20. European Pharmacepoeia Monograph (Particulate Contamination: Visible Particles). The apparatus required consists of a viewing station comprising:
- a matt black panel of appropriate size held in a vertical position
- a non-glare white panel of appropriate size held in a vertical position next to the black panel
- an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels are removed from the container and the outside washed and dried. The container is gently swirled or inverted, ensuring that air bubbles are not introduced, and observed for about 5 s in front of the white panel. The procedure is repeated in front of the black panel. The presence of any particles is recorded.

The visual scores are ranked as follows:

Visual Assessment Scoring Method A
- Visual score 1: clear solution free of particles
- Visual score 2: slight particle formation
- Visual score 3: more significant precipitation Visual Assessment Scoring Method B
- Visual score 1: Clear solution, virtually free of particles
- Visual score 2: ~5 very small particles
- Visual score 3: ~10-20 very small particles
- Visual score 4: 20-50 particles, including larger particles
- Visual score 5: >50 particles, including larger particles Whilst the particles in samples with visual scores 4 and 5 are clearly detectable on casual visual assessment under normal light, samples with visual score 1-3 generally appear as clear solutions on the same assessment. Samples with visual scores 1-3 are considered to be "Pass"; samples with visual score 4-5 are considered to be "Fail".

Example 1—Example Formulations

The following example formulations may be prepared:

Example 1a

| | |
|---|---|
| Insulin lispro | 100 U/ml |
| EDTA | 0.4 mM |
| Sodium phosphate | 2 mM |
| Glycerol | 173 mM |
| m-Cresol | 29 mM |
| Ionic zinc (as $ZnCl_2$) | 0.3 mM |
| Polysorbate 80 | 20 µg/ml |
| Water for injection | qs |
| Residual NaCl | Acidification and subsequent neutralisation during preparation results in formation of 2-4 mM NaCl | pH adjusted to 7.4

Example 1b

| | |
|---|---|
| Insulin lispro | 500 U/ml |
| EDTA | 0.4 mM |
| Sodium phosphate | 2 mM |
| Glycerol | 173 mM |
| m-Cresol | 29 mM |
| Ionic zinc (as $ZnCl_2$) | 0.3 mM |
| Polysorbate 80 | 20 µg/ml |
| Water for injection | qs |
| Residual NaCl | Acidification and subsequent neutralisation during preparation results in formation of 2-4 mM NaCl | pH adjusted to 7.4

Example 1c

| | |
|---|---|
| Insulin lispro | 100 U/ml |
| EDTA | 0.6 mM |
| Sodium phosphate | 2 mM |
| Glycerol | 173 mM |
| m-Cresol | 29 mM |
| Ionic zinc (as $ZnCl_2$) | 0.3 mM |
| Polysorbate 80 | 20 μg/ml |
| Water for injection | qs |
| Residual NaCl | Acidification and subsequent neutralisation during preparation results in formation of 2-4 mM NaCl | pH adjusted to 7.4

Method for Preparation for the Above Formulations:

Insulin powder is added to water and HCl is added until the powder is fully dissolved (pH has to be <3 in order to achieve full dissolution). ZnCl2 is added to the required level. Once dissolved, pH is adjusted to approximately 7 and volume is adjusted with water so that the insulin concentration is 2× the required concentration. The composition is then mixed 1:1 (v/v) with a mixture of additional excipients (all at 2× the required concentration).

Example 2—Stability of Formulations of the Invention

The effect of different surfactants was tested on stability of insulin lispro (100 U/ml) in the presence of 0.4 mM EDTA. The visual assessment method described in General Methods was used. All compositions contained: glycerol (173 mM), m-cresol (29 mM), sodium phosphate (2 mM) and zinc chloride (0.3 mM) and were adjusted to pH 7.4. The control formulation did not contain EDTA; all other formulations contained 0.4 mM EDTA.

The results below (Table 1) show that presence of EDTA in the control formulation resulted in precipitation following incubation at 30° C. for 4 weeks. In addition, the size of the main peak (corresponding to intact insulin) was reduced both on the size-exclusion chromatogram and on RP-HPLC chromatogram compared with the EDTA-free sample. The presence of polysorbate 80 prevented these adverse changes, resulting in stability that was almost comparable with the EDTA-free control. Most of the other samples that contained alternative surfactants also precipitated, some of those to a degree that prevented SEC and RP-HPLC measurement. Some surfactants (dodecyl maltoside, benzethonium chloride and benzalkonium chloride) prevented precipitation, but did not prevent the reduction in size of the main peak on SEC and RP-HPLC chromatograms.

TABLE 1

| Surfactant | Visual assessment (4 weeks at 30° C.) | SEC main peak (4 weeks at 30° C.) | RP-HPLC main peak (4 weeks at 30° C.) |
|---|---|---|---|
| Control (no EDTA, no surfactant) | Clear | 98.54% | 97.70% |
| No surfactant (i.e. control + 0.4 mM EDTA) | Precipitated | 96.72% | 95.78% |
| Polysorbate 80 (20 μg/ml) | Clear | 98.10% | 97.24% |
| Polysorbate 20 (20 μg/ml) | Precipitated | Not analysed due to excessive precipitation | Not analysed due to excessive precipitation |
| Polysorbate 40 (20 μg/ml) | Precipitated | Not analysed due to excessive precipitation | Not analysed due to excessive precipitation |
| Polysorbate 60 (20 μg/ml) | Precipitated | Not analysed due to excessive precipitation | Not analysed due to excessive precipitation |
| Dodecyl maltoside (0.1 mg/ml) | Precipitated | Not analysed due to excessive precipitation | Not analysed due to excessive precipitation |
| Dodecyl maltoside (0.5 mg/ml) | Particles observed | 96.08% | 95.71% |
| Decyl glucopyranoside (0.1 mg/ml) | Precipitated | Not analysed due to excessive precipitation | Not analysed due to excessive precipitation |
| Octyl thioglucopyranoside | Precipitated | Not analysed due to excessive precipitation | Not analysed due to excessive precipitation |
| Lauryldimethylamine oxide (0.1 mg/ml) | Particles observed | Not analysed due to excessive precipitation | Not analysed due to excessive precipitation |
| Benzethonium chloride (20 μg/ml) | Clear | 96.71% | 95.78% |
| Benzalkonium chloride (20 μg/ml) | Clear | 94.47% | 95.36% |

The above data demonstrates the uniqueness of polysorbate 80 amongst other surfactants, including other polysorbates. Of the formulations tested, only the formulations of the invention showed acceptable stability after storage at 30° C. for 4 weeks.

Example 3: Stability of Insulin Aspart Formulations in the Presence of Citrate and Polysorbate 80

The effect of polysorbate 80 on stability of insulin aspart (100 U/ml) in the presence of 22 mM sodium citrate was tested as described in General Methods using Visual Assessment Scoring Method A. All compositions contained: sodium chloride (150 mM), phenol (15.9 mM), m-cresol (15.9 mM), sodium phosphate (2 mM) ionic zinc (19.7 µg/ml, excluding counter-anion, as $ZnCl_2$) and were adjusted to pH 7.4. The control formulation did not contain sodium citrate; all other formulations contained 22 mM sodium citrate. The results (Table 2) below show that presence of sodium citrate to the control formulation resulted in rapid particle formation at 30° C. The presence of polysorbate 80 led to a considerable reduction in the rate of particle formation.

TABLE 2

Visual scores of insulin aspart compositions following storage at 30° C. using Visual Assessment Scoring Method A. Extent of visible precipitation is graded on a scale 1-3; 1 = clear solution free of visible particles; 2 = slight particle formation, 3 = more significant precipitation.

|  | 0 days | 4 days | 7 days | 14 days | 28 days |
|---|---|---|---|---|---|
| Control (i.e. no citrate, no surfactant) | 1 | 1 | 1 | 1 | 1 |
| 22 mM citrate | 1 | 2 | 3 | 3 | 3 |
| 22 mM citrate + 50 µg/ml polysorbate 80 | 1 | 1 | 2 | 2 | 2 |

Example 4—Effect of Polysorbate 80 on the Stability of Insulin Aspart in the Presence of Trisodium Citrate, L-Histidine and Pyrophosphate Stability of insulin aspen (100 U/ml) was investigated in compositions comprising trisodium citrate (22 mM), L-histidine (10 mM) or pyrophosphate (5 mM), both in the presence and in the absence of polysorbate 80. Polysorbate 20 and poloxamer 188 were also tested as comparators. All compositions tested further comprised sodium chloride (150 mM), phenol (15.9 mM), m-cresol (15.9 mM), sodium phosphate (2 mM), ionic zinc (19.7 µg/ml, excluding counter-anion, as $ZnCl_2$) and were adjusted to pH 7.4.

It was shown (Table 3) that the presence of trisodium citrate, L-histidine or pyrophosphate increased considerably the rate of particle formation in formulations of insulin aspart, using the Visual Assessment Scoring Method B. The presence of polysorbate 80 showed a stabilising effect. The ability of poloxamer 188 to mitigate the increase in particle formation rate was shown to be worse than that of polysorbate 80. Polysorbate 20 was not effective at all in this experiment.

TABLE 3

Visual scores of insulin aspart (100 U/ml) formulations using Visual Assessment Scoring Method B following storage at 30° C.

| Chelating agent | Surfactant (all at 50 µg/ml) | 0 days | 4 days | 7 days | 14 days | 28 days |
|---|---|---|---|---|---|---|
| None | None | 1 | 1 | 1 | 1 | 1 |
| Trisodium citrate (22 mM) | None | 1 | 3 | 4 | 5 | 5 |
| Trisodium citrate (22 mM) | Polysorbate 80 | 1 | 1 | 3 | 3 | 3 |
| Trisodium citrate (22 mM) | Polysorbate 20 | 1 | 3 | 4 | 5 | 5 |
| Trisodium citrate (22 mM) | Poloxamer 188 | 1 | 2 | 4 | 5 | 5 |
| L-Histidine (10 mM) | None | 1 | 4 | 5 | 5 | 5 |
| L-Histidine (10 mM) | Polysorbate 80 | 1 | 4 | 4 | 4 | 5 |
| L-Histidine (10 mM) | Polysorbate 20 | 1 | 4 | 5 | 5 | 5 |
| L-Histidine (10 mM) | Poloxamer 188 | 1 | 4 | 4 | 5 | 5 |
| Pyrophosphate (5 mM) | None | 1 | 5 | 5 | 5 | 5 |
| Pyrophosphate (5 mM) | Polysorbate 80 | 1 | 4 | 5 | 5 | 5 |
| Pyrophosphate (5 mM) | Polysorbate 20 | 1 | 5 | 5 | 5 | 5 |
| Pyrophosphate (5 mM) | Poloxamer 188 | 1 | 5 | 5 | 5 | 5 |

Example 5—Effect of Polysorbate 80 on the Stability of Insulin Lispro in the Presence of Citric Acid Stability of insulin lispro (100 U/ml) was investigated in formulations comprising citric acid (22 mM), both in the presence and in the absence of polysorbate 80. Polysorbate 20 and poloxamer 188 were also tested as comparators. All formulations contained: phenol (15.9 mM), m-cresol (15.9 mM), sodium phosphate (2 mM), ionic zinc (19.7 µg/ml, excluding counter-anion, as $ZnCl_2$) and were adjusted to pH 7.8. Formulations contained glycerol (174 mM) as a tonicity modifier.

It was shown (Table 4) that the presence of citric acid (22 mM) resulted in an increased formation of particles in compositions of insulin lispro in the absence of polysorbate 80 or poloxamer 188, using the Visual Assessment Scoring Method B. The presence of polysorbate 80 appeared to mitigate the destabilising effect. The stabilising effects of polysorbate 20 and poloxamer 188 were notably weaker than that of polysorbate 80

TABLE 4

Visual scores of insulin lispro (100 U/ml) formulations using Visual
Assessment Scoring Method B following storage at indicated temperatures.

| Citric acid (mM) | Surfactant | Tonicity modifier | T = 0 weeks | 2-8° C. (8 weeks) | 30° C. (4 weeks) | 30° C. (8 weeks) | 37° C. (4 weeks) |
|---|---|---|---|---|---|---|---|
| 0 mM | None | Glycerol (174 mM) | 1 | 1 | 1 | 1 | 2 |
| 22 mM | None | Glycerol (174 mM) | 1 | 1 | 4 | 5 | 5 |
| 22 mM | Polysorbate 80 (50 μg/ml) | Glycerol (174 mM) | 1 | 1 | 2 | 2 | 3 |
| 22 mM | Polysorbate 20 (50 μg/ml) | Glycerol (174 mM) | 1 | 1 | 3 | 4 | 4 |
| 22 mM | Poloxamer 188 (50 μg/ml) | Glycerol (174 mM) | 1 | 1 | 4 | 4 | 5 |

Example 6—Effect of Polysorbate 80 on the Stability of Insulin Aspart (1000 U/Ml) in the Presence of Trisodium Citrate, L-Histidine and Pyrophosphate Stability of insulin aspart (1000 U/ml) was investigated in formulations comprising trisodium citrate (44 mM), L-histidine (22 mM) or pyrophosphate (22 mM), both in the presence and in the absence of polysorbate 80. All compositions further comprised phenol (15.9 mM), m-cresol (15.9 mM), sodium phosphate (2 mM), glycerol (174 mM), sodium chloride (10 mM) and ionic zinc (197 μg/ml, excluding counter-anion, as $ZnCl_2$) and were adjusted to pH 7.4.

It was shown (Table 5) that the presence of trisodium citrate, L-histidine or pyrophosphate resulted in a considerable increase in the rate of particle formation of insulin aspart, using the Visual Assessment Scoring Method B. The presence of polysorbate 80 showed a stabilising effect.

Example 7: Investigation of the Optimal Concentration of Polysorbate 80 on the Stability of Insulin Aspart (1000 U/Ml) in the Presence of Different Concentrations of Citric Acid The stability of insulin aspart (1000 U/ml) was investigated in the presence of different concentrations of citric acid and different concentrations of polysorbate 80. All formulations tested further comprised phenol (15.9 mM), m-cresol (15.9 mM), sodium phosphate (2 mM), glycerol (174 mM) and ionic zinc (197 μg/ml, excluding counter-anion, as $ZnCl_2$) and were adjusted to pH 7.8. Three concentrations of citric acid (44, 66 and 88 mM) and four concentrations of each non-ionic surfactant were tested as well as corresponding surfactant-free compositions.

The rate of particle formation in formulations of insulin aspart (1000 U/ml) was found to be proportional to citric acid concentration in the range between 44 and 88 mM and, thus, the lower concentration of citric acid (44 mM is more suitable in this experiment (Table 6). The presence of polysorbate 80 led to a reduction in the rate of particle formation. The higher concentrations (0.3 and 0.5 mg/ml) of polysorbate 80 showed a greater ability to reduce the particle formation rate than the lower concentrations (0.05 and 0.1 mg/ml).

TABLE 5

Visual scores of insulin aspart (1000 U/ml) formulations using Visual
Assessment Scoring Method B following storage at indicated temperatures.

| Chelating agent | Surfactant | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|
| None | None | 24.16 | 1 | 1 | 2 | 2 | 3 |
| Citrate (44 mM) | None | 24.16 | 1 | 2 | 4 | 5 | 5 |
| Citrate (44 mM) | Polysorbate 80 (50 μg/ml) | 24.16 | 1 | 2 | 1 | 3 | 5 |
| Histidine (22 mM) | None | 24.16 | 1 | 2 | 4 | 5 | 5 |
| Histidine (22 mM) | Polysorbate 80 (50 μg/ml) | 24.16 | 1 | 2 | 4 | 5 | 4 |
| Pyrophosphate (22 mM) | None | 24.16 | 1 | 3 | 5 | 5 | 5 |
| Pyrophosphate (22 mM) | Polysorbate 80 (50 μg/ml) | 24.16 | 1 | 1 | 4 | 5 | 5 |

*ionic strength calculation takes into account all ions in the formulation except for the zinc binding species (trisodium citrate, L-histidine or pyrophosphate) and the insulin compound using formula I.

TABLE 6

Visual scores of insulin aspart (1000 U/ml) formulations using Visual Assessment Scoring Method B following storage at indicated temperatures.

| Citric acid | Polysorbate 80 (mg/ml) | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|---|
| 44 mM | 0 | 14.84 | 1 | 3 | 4 | 5 | 5 |
| 44 mM | 0.05 | 14.84 | 1 | 3 | 2 | 3 | 4 |
| 44 mM | 0.1 | 14.84 | 1 | 2 | 2 | 3 | 4 |
| 44 mM | 0.3 | 14.84 | 1 | 2 | 2 | 3 | 4 |
| 44 mM | 0.5 | 14.84 | 1 | 1 | 1 | 3 | 4 |
| 66 mM | 0 | 14.84 | 1 | 5 | 5 | 5 | 5 |
| 66 mM | 0.05 | 14.84 | 1 | 5 | 4 | 5 | 5 |
| 66 mM | 0.1 | 14.84 | 1 | 5 | 4 | 5 | 5 |
| 66 mM | 0.3 | 14.84 | 1 | 4 | 3 | 4 | 4 |
| 66 mM | 0.5 | 14.84 | 1 | 4 | 4 | 5 | 5 |
| 88 mM | 0 | 14.84 | 1 | 5 | 5 | 5 | 5 |
| 88 mM | 0.05 | 14.84 | 1 | 5 | 4 | 5 | 5 |
| 88 mM | 0.1 | 14.84 | 1 | 5 | 4 | 4 | 5 |
| 88 mM | 0.3 | 14.84 | 1 | 5 | 3 | 4 | 5 |
| 88 mM | 0.5 | 14.84 | 1 | 5 | 3 | 5 | 5 |

*ionic strength calculation takes into account all ions in the formulation except for the zinc binding species (citric acid) and the insulin compound using formula I.

Abbreviations

EDTA ethylenediaminetetraacetate
EGTA ethyleneglycoltetraacetate
HPLC high performance liquid chromatography
HMWS high molecular weight species
RP reverse phase
SEC size-exclusion chromatography Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

| Sequence Listing: |
|---|
| SEQ ID NO: 1: GIVEQCCTSICSLYQLENYCN |
| SEQ ID NO: 2: FVNQHLCGSHLVEALYLVCGERGFFYTPKT |
| SEQ ID NO: 3: FVNQHLCGSHLVEALYLVCGERGFFYTKPT |
| SEQ ID NO: 4: FVNQHLCGSHLVEALYLVCGERGFFYTDKT |
| SEQ ID NO: 5: FVKQHLCGSHLVEALYLVCGERGFFYTPET |

The invention claimed is:

1. An aqueous liquid pharmaceutical formulation comprising
    an insulin analogue at a concentration of 100-1000 U/ml,
    ionic zinc at a concentration of 0.25-1% by weight of zinc based on the weight of the insulin analogue in the formulation,
    citrate as a chelating agent at a concentration of 10-50 mM and
    polysorbate 80 at a concentration of 0.05-0.5 mg/ml,
wherein fewer than 20 particles are detectable in the formulation after 8 weeks at 30° C. using the method described in the 2.9.20 European Pharmacopoeia Monograph.

2. The formulation according to claim 1 comprising insulin lispro as an insulin analogue.

3. The formulation according to claim 1 comprising insulin aspart as an insulin analogue.

4. The formulation according to claim 1 comprising insulin glulisine as an insulin analogue.

5. The formulation according to claim 1, wherein the ionic zinc is present at a concentration of 0.35-0.75% by weight of zinc based on the weight of insulin analogue in the formulation.

6. The formulation according to claim 5, wherein the ionic zinc is present at a concentration of 0.45-0.6% by weight of zinc based on the weight of insulin analogue in the formulation.

7. The formulation according to claim 1, wherein the citrate is present at a concentration of 20-50 mM.

8. The formulation according to claim 1, wherein the citrate is present at a concentration of 30-50 mM.

9. The formulation according to claim 1, further comprising an uncharged tonicity modifier.

10. The formulation according to claim 9, wherein the uncharged tonicity modifier is selected from the group consisting of trehalose, mannitol, glycerol or 1,2-propanediol.

11. The formulation according to claim 10, wherein the uncharged tonicity modifier is glycerol.

12. The formulation according to claim 1, wherein the composition is isotonic.

13. The formulation according to claim 1, wherein the pH is in the range 5.5 to 9.0.

14. The formulation according to claim 13, wherein the pH is in the range 7.0 to 7.5.

15. The formulation according to claim 13, wherein the pH is in the range 7.6 to 8.0.

16. The formulation according to claim 1, further comprising a preservative.

17. The formulation according to claim 16, wherein the preservative is selected from the group consisting of phenol, m-cresol, chlorocresol, benzyl alcohol, propylparaben, methylparaben, benzalkonium chloride and benzethonium chloride.

18. The formulation according to claim 1, wherein the ionic strength of the formulation is less than 300 mM.

19. A method of treatment of diabetes mellitus which comprises administering to a subject in need thereof an effective amount of a formulation according to claim 1.

20. A container comprising one dose or a plurality of doses of the formulation according to claim 1 and an injection needle.

21. The formulation according to claim 1, wherein citrate as chelating agent is present at a concentration of 22 mM.

22. The formulation according to claim 1 wherein citrate as chelating agent is present at a concentration of 44 mM.

23. The formulation according to claim 1, wherein the polysorbate 80 is present at a concentration of 0.3-0.5 mg/ml.

24. The formulation according to claim 1 which further comprises arginine and proline.

* * * * *